US010655156B2

(12) United States Patent
Gupta et al.

(10) Patent No.: US 10,655,156 B2
(45) Date of Patent: *May 19, 2020

(54) OVEREXPRESSION OF N-GLYCOSYLATION PATHWAY REGULATORS TO MODULATE GLYCOSYLATION OF RECOMBINANT PROTEINS

(71) Applicant: AMGEN INC., Thousand Oaks, CA (US)

(72) Inventors: Shivani Gupta, Thousand Oaks, CA (US); Sohye Kang, Camarillo, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/261,311

(22) Filed: Jan. 29, 2019

(65) Prior Publication Data

US 2019/0153496 A1 May 23, 2019

Related U.S. Application Data

(60) Continuation of application No. 16/130,879, filed on Sep. 13, 2018, now Pat. No. 10,227,627, which is a division of application No. 15/115,615, filed as application No. PCT/US2014/069744 on Dec. 11, 2014, now Pat. No. 10,106,829.

(60) Provisional application No. 61/933,137, filed on Jan. 29, 2014.

(51) Int. Cl.
*A61K 38/14* (2006.01)
*C12Q 1/48* (2006.01)
*C12P 21/00* (2006.01)
*C07K 16/00* (2006.01)
*C07K 14/705* (2006.01)
*C12N 9/10* (2006.01)
*C12N 15/85* (2006.01)

(52) U.S. Cl.
CPC .......... *C12P 21/005* (2013.01); *C07K 14/705* (2013.01); *C07K 16/00* (2013.01); *C12N 9/1051* (2013.01); *C12N 15/85* (2013.01); *C12Y 204/01101* (2013.01); *C12Y 204/01143* (2013.01); *C07K 2317/41* (2013.01)

(58) Field of Classification Search
CPC ..... C12P 21/005; C07K 14/705; C07K 16/00; C12Y 204/01143; C12Y 204/01102
See application file for complete search history.

(56) References Cited

U.S. PATENT DOCUMENTS

| 4,695,623 | A | 9/1987 | Stabinsky |
| 4,897,471 | A | 1/1990 | Stabinsky |
| 4,968,607 | A | 11/1990 | Dower et al. |
| 5,075,222 | A | 12/1991 | Hannum et al. |
| 5,149,792 | A | 9/1992 | Thomason |
| 5,272,064 | A | 12/1993 | Thomason |
| 5,395,760 | A | 3/1995 | Smith et al. |
| 5,610,279 | A | 3/1997 | Brockhaus et al. |
| 5,672,502 | A | 9/1997 | Birch et al. |
| 5,767,064 | A | 6/1998 | Sims et al. |
| 5,856,296 | A | 1/1999 | Mosley et al. |
| 5,877,293 | A | 3/1999 | Adair et al. |
| 5,886,152 | A | 3/1999 | Nakatani et al. |
| 5,981,713 | A | 11/1999 | Colotta et al. |
| 6,015,938 | A | 1/2000 | Boyle et al. |
| 6,054,297 | A | 4/2000 | Carter et al. |
| 6,096,728 | A | 8/2000 | Collins et al. |
| 6,204,363 | B1 | 3/2001 | Zsebo et al. |
| 6,235,883 | B1 | 5/2001 | Jakobovits et al. |
| 6,271,349 | B1 | 8/2001 | Dougall et al. |
| 6,337,072 | B1 | 1/2002 | Ford et al. |
| 6,544,424 | B1 | 4/2003 | Shevitz |
| 6,696,245 | B2 | 2/2004 | Winter et al. |
| 6,846,634 | B1 | 1/2005 | Tomlinson et al. |
| 8,053,238 | B2 | 11/2011 | Jin et al. |
| 2003/0039958 | A1 | 2/2003 | Holt et al. |
| 2004/0009507 | A1 | 1/2004 | Winter et al. |
| 2004/0038291 | A2 | 2/2004 | Tomlinson et al. |
| 2004/0202995 | A1 | 10/2004 | de Wildt et al. |
| 2005/0202512 | A1 | 9/2005 | Tomlinson et al. |
| 2006/0140934 | A1 | 6/2006 | Gegg et al. |
| 2013/0040897 | A1 | 2/2013 | Aebi et al. |
| 2013/0231255 | A1 | 9/2013 | Collins et al. |

FOREIGN PATENT DOCUMENTS

| AU | 588819 B2 | 9/1989 |
| EP | 0367566 B1 | 5/1997 |
| EP | 0460846 B1 | 2/2002 |
| WO | WO 1994/10308 A1 | 5/1994 |
| WO | WO 1997/001633 A1 | 1/1997 |
| WO | WO 2001/036637 A1 | 5/2001 |
| WO | WO 2008/154014 A2 | 12/2008 |
| WO | WO 2010/049177 A1 | 5/2010 |
| WO | WO 2011/134643 A1 | 11/2011 |
| WO | WO 2012/145682 A1 | 10/2012 |

OTHER PUBLICATIONS

Ahn et al., Effect of culture temperature on erythropoietin production and glycosylation in a perfusion culture of recombinant CHO cells, *Biotechnol Bioeng* (2008) 101(6):1234-1244.
Bird et al., Single-Chain Antigen-Binding Proteins, *Science* (1988) 242:423-426.
Brasel et al., Hematologic Effects of flt3 Ligand In Vivo in Mice, *Blood* (1996) 88:2004-2012.
Catapano et al., "Bioreactor Design and Scale-Up," *Cell and Tissue Reaction Engineering: Principles and Practice*, Springer-Verlag Berlin Heidelberg (2009), 5:173-259.
Chothia et al., Canonical Structure for the Hypervariable Regions of Immunoglobulins, *J. Mol.Biol.* (1987) 196:901-917.
Chothia et al., Conformations of Immunoglobulin Hypervariable Regions, *Nature* (1989) 342:878-883.

(Continued)

Primary Examiner — Maryam Monshipouri
(74) Attorney, Agent, or Firm — Scott Siera

(57) ABSTRACT

Methods of modulating the properties of a cell culture expressing a protein of interest are provided. In various embodiments the methods relate to the overexpression of proteins involved in the N-glycosylation pathway.

21 Claims, 3 Drawing Sheets

(56) References Cited

OTHER PUBLICATIONS

Dicker & Strasser, Using Glyco-Engineering to Produce Therapeutic Proteins, Expert Opinion on Biological Therapy (2015), 15:10, 1501-1516.
Do et al., Mechanism of BLyS Action in B Cell Immunity, *Cytokine Growth Factor Rev.* (2002), 13(1): 19-25.
Furey, Scale-Up of a Cell Culture Perfusion Process—A Low-Shear Filtration System that Inhibits Filter-Membrane Fouling, *Gen. Eng. News* (2002) 22(7):62-63.
Goetze et al., High-Mannose Glycans on the Fc Region of Therapeutic IgG Antibodies Increase Serum Clearance in Humans, *Glycobiology*, Oxford University Press (2011), 21(7): 949-959.
Hakansson et al., Crystal Structure of the Trimeric α-Helical Coiled-Coil and the Three Lectin Domains of Human Lung Surfactant Protein D, *Structure* (1999), 7:255-64.
Harbury et al., A Switch Between Two-, Three-, and Four-Stranded Coiled Coils in GCN4 Leucine Zipper Mutants, *Science* (1993), 262:1401-05.
Harbury et al., Crystal Structure of an Isoleucine-Zipper Trimer, *Nature* (1994), 371:80-83.
Hemmoranta et al., N-Glycans Structures and Associated Gene Expression Reflect the Characteristic N-Glycosylation Pattern of Human Hemotopoietic Stem and Progenitor Cells, *Experimental Hematology*, Elsevier Inc. (2007) 35(8):1279-1292.
Hollinger et al., "Diabodies": Small Bivalent and Bispecific Antibody Fragments, *Proc. Natl. Acad. Sci.* (1993) 90:6444-6448.
Honegger et al., Yet Another Numbering Scheme for Immunoglobulin Variable Domains: An Automatic Modeling and Analysis Tool, *J. Mol. Biol.* (2001) 309:657-670.
Huston et al., Protein Engineering of Antibody Binding Sites: Recovery of Specific Activity in an Anti-Digoxin Single-Chain Fv Analogue Produced in *Escherichia coli*, *Proc. Natl. Acad. Sci. USA* (1988) 85:5879-5883.
Kaufman et al., Synthesis, Processing, and Secretion of Recombinant Human Factor VIII Expressed in Mammalian Cells, *J. Biol Chem* (1988) 263:6352-6362.
Kaufman, Selection and Coamplification of Heterologous Genes in Mammalian Cells, *Meth Enzymol* (1990) 185:537-566.
Korndorfer et al., Crystallographic Analysis of an "Anticalin" with Tailored Specificity for Fluorescein Reveals High Structural Plasticity of the Lipocalin Loop Region, *Proteins: Structure, Function, and Bioinformatics* (2003), 53:121-129.
Kuystermans et al., "Bioreactor Systems for Producing Antibody from Mammalian Cells," M. Al-Rubeai (ed.), *Antibody Expression and Production, Cell Engineering* (2011) 7:25-52.
Lovejoy et al., Crystal Structure of a Synthetic Triple-Stranded α-Helical Bundle, *Science* (1993), 259:1288-1293.
Maisonpierre et al., Angiopoietin-2, a Natural Antagonist for Tie2 That Disrupts in vivo Angiogenesis, *Science* (1997) 277(5322):55-60.
Mckinnon et al., Expression, Purification and Characterization of Secreted Recombinant Human Insulin-Like Growth Factor-I (IGF-I) and the Potent Variant Des(1-3)IGF-I in Chinese Hamster Ovary Cells, *J Mol Endocrinol* (1991) 6:231-239.
Milstein et al., Hybrid Hybridomas and Their Use in Immunohistochemistry, *Nature* (1983) 305:537-540.
NCBI Accession No. NM_006682.
Poljak et al., Production and Structure of Diabodies, *Structure* (1994) 2:1121-1123.
Roque et al., Antibodies and genetically engineered related molecules: production and purification, *Biotechnol Prog*, (2004) 20:639-654.
Rüegg et al., Sequence of Human Transcript Expressed in T-Lymphocytes and Encoding a Fibrinogen-Like Protein, *Gene* (1995)160:257-262.
Stettler, et al., New Disposable Tubes for Rapid and Precise Biomass Assessment for Suspension Cultures of Mammalian Cells, *Biotechnol Bioeng.* (2006) 95(6):1228-1233.
Tomiya et al., Complex-Type Biantennary N-Glycans of Recombinant Human Transferrin from Trichoplusia Ni Insect Cells Expressing Mammalian Beta-1, 4-Galactosyltranserase and Beta-1, 2-N-Acetylglucosaminyltransferase II, *Glycobiology*, Oxford University Press (2003) 13(1):23-34.
Urlaub et al., Isolation of Chinese Hamster Cell Mutants Deficient in Dihydrofolate Reductase Activity, *Proc Natl Acad Sci USA* (1980) 77: 4216-4220.
Voisard et al., Potential of Cell Retention Techniques for Large-Scale High Density Perfusion Culture of Suspended Mammalian Cells, *Biotechnol. Bioeng.* (2003), 82:751-65.
Ward et al., Binding Activities of a Repertoire of a Single Immunoglobulin Variable Domains Secreted from *Escherichia coli*, *Nature* (1989) 341:544-546.
Wong et al., Impact of dynamic online fed-batch strategies on metabolism, productivity and N-glycosylation quality in CHO cell cultures, *Biotechnol Bioeng* (2005) 89(2):164-177.
Wood et al., High Level Synthesis of Immunoglobulins in Chinese Hamster Ovary Cells, (1990), *J. Immunol.* (1990) 145:3011-3016.
Wright et al., Effect of glycosylation on antibody function: implications for genetic engineering, *Trends in Biotechnol* (1997) 15(1):26-32.
Yu et al., Production, Characterization and Pharmacokinetic Properties of Antibodies with N-Linked Mannose-5 Glycans, *MAbs* (2012), 4:475-487.

OVEREXPRESSION OF N-GLYCOSYLATION PATHWAY REGULATORS TO MODULATE GLYCOSYLATION OF RECOMBINANT PROTEINS

CROSS REFERENCE TO RELATED APPLICATIONS

This application is a continuation of pending U.S. application Ser. No. 16/130,879, filed Sep. 13, 2018, which is a divisional of U.S. application Ser. No. 15/115,615, filed on Jul. 29, 2016, now issued as U.S. Pat. No. 10,106,829 on Oct. 23, 2018; which is a 371 of International Patent Appl. No. PCT/US2014/069744, having an international filing date of Dec. 11, 2014; which claims the benefit of U.S. Provisional Application No. 61/933,137 filed Jan. 29, 2014, all of which are incorporated by reference herein.

FIELD OF THE INVENTION

The present invention relates generally to processes for modulating one or more properties of a recombinant protein produced by cell culture, including mammalian cell cultures such as CHO cell cultures.

BACKGROUND OF THE INVENTION

Glycosylation is a common post-translational modification in mammalian cells; both normal human immunoglobulins and therapeutic monoclonal antibodies (mAbs) produced in Chinese hamster ovary (CHO) cells are glycoproteins. Both pharmacokinetic properties and effector functions of therapeutic mAbs can be affected by glycosylation. Terminal sugars such as fucose and galactose may affect antibody-dependent cellular cytoxicity (ADCC) and complement-dependent cytoxicity (CDC; Wright, A. and S. L. Morrison, *Trends Biotechnol* (1997) 15:26-32). High mannose glycans may increase serum clearance of certain mAbs, thus potentially affecting efficacy (Goetze, et al., (2011) *Glycobiology* 21:949-59). Alternatively, high mannose glycoforms can increase the affinity of antibodies for Fc gamma III receptor, thus increasing ADCC activity of certain antibodies (Yu, et al. (2012) *MAbs* 4:475-87). Thus for each recombinant mAb, a certain glycosylation profile that best supports the therapeutic potential of the mAb needs to be maintained.

Methods for manipulating high mannose glycoform content of a protein in cell culture include changes in media compositions, osmolality, pH, temperature, etc. (Yu, et al., supra, Pacis et al., supra, Chee Furng Wong et al. (2005) *Biotechnol Bioeng* 89:164-177; Ahn, et al. (2008) *Biotechnol Bioeng* 101:1234-44). The effectiveness of these methods is specific to cell lines, molecule types and media environment and is typically obtained by trial and error. Additionally, these methods tend to also alter antibody productivity, cell culture behavior and other antibody quality attributes.

There still exists a need to identify a mechanism which can regulate high mannose glycoforms (particularly Mannose 5), on mAbs without compromising CHO production culture performance and antibody yield. Such a method would benefit the process development of therapeutic proteins. The invention provides a method that regulates high mannose glycoform content by manipulating levels of expression of proteins involved in the N-glycosylation pathway.

SUMMARY OF THE INVENTION

The present invention provides a method for regulating the high mannose glycoform content of a recombinant protein during a mammalian cell culture process comprising transforming a host cell to overexpress a protein that is involved in the N-glycosylation pathway. The invention further provides a method for decreasing the high mannose glycoform content of a recombinant protein during the mammalian cell culture process. In one embodiment, the protein is N-acetyl-glucosaminyltransferase-1 (encoded by Mgat1); in another embodiment of the invention, the protein is N-acetyl-glucosaminyltransferase-2 (encoded by Mgat2). In a further embodiment of the invention, the protein is a UDP-Galactose transporter (encoded by Slc35a2).

Additional embodiments of the invention include transformation of the host cell to overexpress two or more proteins involved in the N-glycosylation pathway, including combinations of the aforementioned proteins. In one embodiment, the host cell is transformed with Mgat1 and Mgat2; in other embodiments, the host cell is transformed with Mgat1 and Slc35a2, with Mgat2 and Slc35a2, or with Mgat1, Mgat2 and Slc35a2.

The invention also provides for transfection of a host cell line that has been previously transfected to express a recombinant protein. In one embodiment, the recombinant protein is a protein comprising an antibody Fc region. Further embodiment includes host cells that express a recombinant protein selected from the group consisting of Fc fusion proteins, antibodies, immunoglobulins, and peptibodies.

In a further embodiment, a host cell is first transfected to overexpress one or more of Mgat1, Mgat2 and Slc35a2, and then is transfected to express a recombinant protein. In one embodiment, the recombinant protein is a protein comprising an antibody Fc region. Further embodiment includes expression of a recombinant protein selected from the group consisting of Fc fusion proteins, antibodies, immunoglobulins, and peptibodies.

Optionally, the invention further comprises a step of harvesting the recombinant protein produced by the cell culture. In a further embodiment the recombinant protein produced by the cell culture is purified and formulated in a pharmaceutically acceptable formulation.

In a further embodiment the high mannose glycoform content of a recombinant protein is decreased compared to that produced by a culture where the cells are not manipulated by transfection to overexpress a protein involved in N-linked glycosylation. In one embodiment the high mannose glycan species is Mannose 5 (Man5). In another embodiment, the high mannose glycan species is Mannose 6 (Man6), Mannose 7 (Man7), Mannose 8 (including Mannose 8a and 8b; Man8a and 8b, or Mannose 9 (Man9). In a further embodiment the high mannose glycan species comprise a mixture of Man5, Man6, Man7, Man8a, Man8b, and/or Man9.

The invention provides a further embodiment in which the high mannose glycoform content of a recombinant protein is reduced. In a further embodiment, the high mannose glycoform content of a recombinant protein is less than or equal to 5%. In another embodiment, the high mannose glycoform content of a recombinant protein is less than or equal to 10%. In a further embodiment, the high mannose glycoform content of a recombinant protein produced by a cell culture of the invention is less than 6, 7, 8, 9, or 10 percent. In yet another embodiment, the high mannose glycoform content of a recombinant protein produced by a cell culture of the invention is 0.5, 1, 2, 3, 4, or 5%. Further embodiments include high mannose glycoform content of less than 12%, less than 15%, less than 20%, or less than 30%, 40% or 50%.

Additional embodiments include the use of a batch or fed-batch culture and the use of a perfusion culture. In one embodiment, the culture is perfused using alternating tangential flow (ATF).

In combination with any of the embodiments of the invention described herein, antifoam may also added into the culture vessel as needed. Alternatively or additionally, 1M Sodium Carbonate or another suitable base is used to maintain pH at the desired setpoint.

As described herein, in one aspect of the invention the cell culture may be maintained by perfusion. In one embodiment perfusion begins on or about day 1 to on or about day 9 of the cell culture. In a related embodiment perfusion begins on or about day 3 to on or about day 7 of the cell culture. In one embodiment perfusion begins when the cells have reached a production phase. In further embodiments of the invention, perfusion is accomplished by alternating tangential flow. In a related embodiment the perfusion is accomplished by alternating tangential flow using an ultrafilter or a microfilter.

A further embodiment of the invention provides continuous perfusion; in yet a further embodiment the rate of perfusion is constant. One embodiment of the invention provides perfusion performed at a rate of less than or equal to 1.0 working volumes per day. In a related embodiment perfusion is performed at a rate that increases during the production phase from 0.25 working volume per day to 1.0 working volume per day during the cell culture. In another related embodiment perfusion is performed at a rate that reaches 1.0 working volume per day on day 9 to day 11 of the cell culture. In another related embodiment perfusion is performed at a rate that reaches 1.0 working volume per day on day 10 of the cell culture.

In one embodiment the cell culture receives bolus cell culture media feeds prior to days 3-7 of the culture.

In yet another aspect of the invention, the cell culture is maintained by fed batch. In one embodiment of a fed batch culture, the culture is fed three times during production. In a further embodiment, the culture is fed on a day between day two and four, on a day between day 5 and 7, and on a day between day 8 and 10. Another embodiment provides a fed batch method in which the culture is fed four times during production. In a still further embodiment, the culture is fed on a day between day two and four, on a day between day 5 and 6, on a day between day 7 and 8, and on a day between day 8 and 10 or later.

According to one embodiment of the invention, the mammalian cell culture is established by inoculating the bioreactor with at least $0.5 \times 10^6$ to $3.0 \times 10^6$ cells/mL in a serum-free culture media. In an alternate or further embodiment the mammalian cell culture is established by inoculating the bioreactor with at least $0.5 \times 10^6$ to $1.5 \times 10^6$ cells/mL in a serum-free culture media.

The invention may further comprise a temperature shift during the culture. In one embodiment the temperature shift is from 36° C. to 31° C. In one embodiment the invention further comprises a temperature shift from 36° C. to 33° C. In a related embodiment the temperature shift occurs at the transition between the growth phase and production phase. In a related embodiment the temperature shift occurs during the production phase.

In another embodiment the invention further comprises inducing cell growth-arrest by L-asparagine starvation followed by perfusion with a serum-free perfusion media having an L-asparagine concentration of 5 mM or less. In another embodiment the invention further comprises inducing cell growth-arrest by perfusion with a serum-free perfusion media having an L-asparagine concentration of 5 mM or less. In a related embodiment the concentration of L-asparagine in the serum-free perfusion media is less than or equal to 5 mM. In a related embodiment the concentration of L-asparagine in the serum-free perfusion media is less than or equal to 4.0 mM. In a related embodiment the concentration of L-asparagine in the serum-free perfusion media is less than or equal to 3.0 mM. In a related embodiment the concentration of L-asparagine in the serum-free perfusion media is less than or equal to 2.0 mM. In a related embodiment the concentration of L-asparagine in the serum-free perfusion media is less than or equal to 1.0 mM. In a related embodiment the concentration of L-asparagine in the serum-free perfusion media is 0 mM. In a related embodiment the L-asparagine concentration of the cell culture media is monitored prior to and during L-asparagine starvation.

In yet another embodiment the invention comprises that the packed cell volume during a production phase is less than or equal to 35%. In a related embodiment the packed cell volume is less than or equal to 35%. In a related embodiment the packed cell volume is less than or equal to 30%.

In a related embodiment the viable cell density of the mammalian cell culture at a packed cell volume less than or equal to 35% is $10 \times 10^6$ viable cells/ml to $80 \times 10^6$ viable cells/ml. In another embodiment the viable cell density of the mammalian cell culture is $20 \times 10^6$ viable cells/ml to $30 \times 10^6$ viable cells/ml. In yet another embodiment the bioreactor has a capacity of at least 500 L. In yet another embodiment the bioreactor has a capacity of at least 500 L to 2000 L. In yet another embodiment the bioreactor has a capacity of at least 1000 L to 2000 L.

In yet another embodiment the mammalian cells are Chinese Hamster Ovary (CHO) cells. In yet another embodiment the recombinant protein is selected from the group consisting of a human antibody, a humanized antibody, a chimeric antibody, a recombinant fusion protein, or a cytokine.

DETAILED DESCRIPTION OF THE INVENTION

Figure 1:
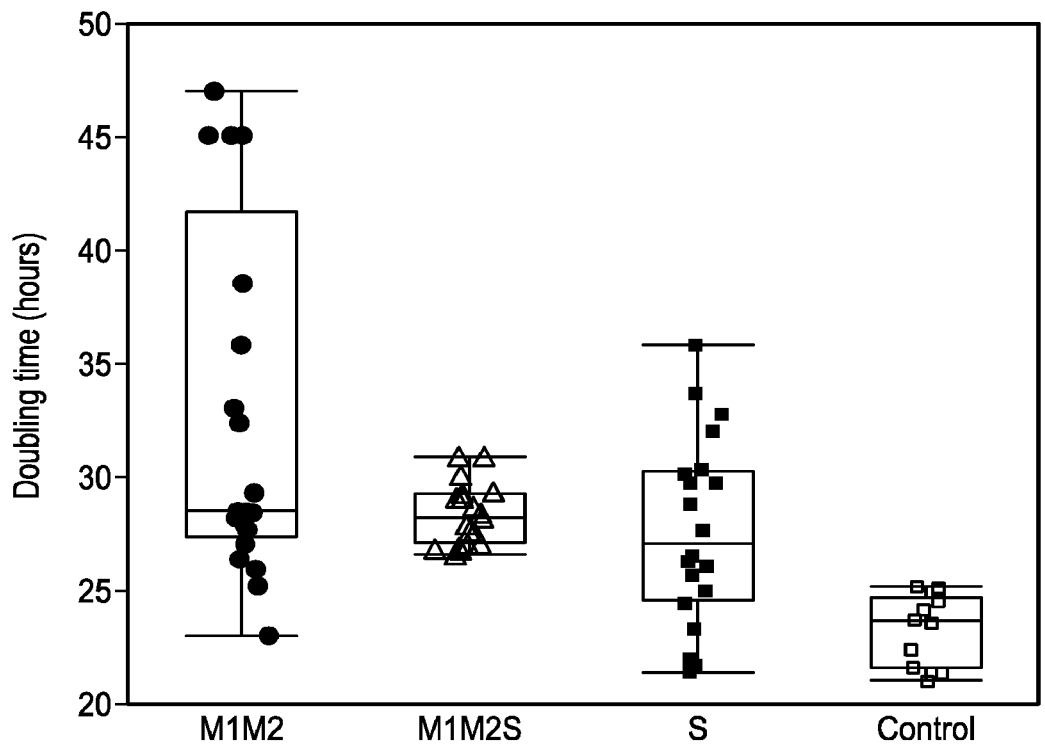
FIG. 1 illustrates clonal variability in doubling time during passaging for the cell lines used for the first set of fed-batch cultures in Example 2. In this Example, cells from a cell line expressing MAb B were transformed to overexpress Mgat1, Mgat2 and/or Slc35A2. M1M2 designates cell lines overexpressing Mgat1 & Mgat2 (individual clones represented by solid circles); M1M2S designates cell lines overexpressing Mgat1, Mgat2 and Slc35a2 (individual clones represented by open triangles); and S designates cell lines overexpressing Slc35A2 (individual clones represented by solid squares). Control cells (individual clones represented by open squares) were transformed with empty vector. The central box spans from the first quartile (Q1) to the third quartile (Q3) and the height of the box is Interquartile range (IQR), the band inside the box is the median, the top whisker extends from Q3 to the largest value falling below Q3+1.5IQR or the maximum value if no value is greater than Q3+1.5IQR. The bottom whisker extends from Q1 to the smallest value falling above Q1-1.5IQR or the minimum value if none is less than Q1-1.5IQR.

While the terminology used in this application is standard within the art, definitions of certain terms are provided herein to assure clarity and definiteness in the meaning of the claims. Units, prefixes, and symbols may be denoted in their SI (International System of Units) accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990).

The disclosed methods are applicable to adherent culture or suspension cultures grown in stirred tank reactors (including traditional batch and fed-batch cell cultures, which may but need not comprise a spin filter), perfusion systems (including alternating tangential flow ("ATF") cultures, acoustic perfusion systems, depth filter perfusion systems, and other systems), hollow fiber bioreactors (HFB, which in some cases may be employed in perfusion processes) as well as various other cell culture methods (see, e.g., Tao et al., (2003) *Biotechnol. Bioeng.* 82:751-65; Kuystermans & Al-Rubeai, (2011) "Bioreactor Systems for Producing Antibody from Mammalian Cells" in *Antibody Expression and Production*, Cell Engineering 7:25-52, Al-Rubeai (ed) Springer; Catapano et al., (2009) "Bioreactor Design and Scale-Up" in *Cell and Tissue Reaction Engineering: Principles and Practice*, Eibl et al. (eds) Springer-Verlag, incorporated herein by reference in their entireties).

All documents, or portions of documents, cited in this application, including but not limited to patents, patent applications, articles, books, and treatises, are hereby expressly incorporated by reference. What is described in an embodiment of the invention can be combined with other embodiments of the invention.

Definitions

As used herein, the terms "a" and "an" mean one or more unless specifically indicated otherwise. Further, unless otherwise required by context, singular terms shall include pluralities and plural teams shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The instant disclosure provides methods of modulating the properties of cell cultures expressing a "protein of interest;" "protein of interest" includes naturally occurring proteins, recombinant proteins, and engineered proteins (e.g., proteins that do not occur in nature and which have been designed and/or created by humans). A protein of interest can, but need not be, a protein that is known or suspected to be therapeutically relevant. Particular examples of a protein of interest include antigen binding proteins (as described and defined herein), peptibodies (i.e., a molecule comprising peptide(s) fused either directly or indirectly to other molecules such as an Fc domain of an antibody, where the peptide moiety specifically binds to a desired target; the peptide(s) may be fused to either an Fc region or inserted into an Fc-Loop, or a modified Fc molecule, for example as described in U.S. Patent Application Publication No. US2006/0140934 incorporated herein by reference in its entirety), fusion proteins (e.g., Fc fusion proteins, wherein a Fc fragment is fused to a protein or peptide, including a peptibody), cytokines, growth factors, hormones and other naturally occurring secreted proteins, as well as mutant forms of naturally occurring proteins.

The term "antigen binding protein" is used in its broadest sense and means a protein comprising a portion that binds to an antigen or target and, optionally, a scaffold or framework portion that allows the antigen binding portion to adopt a conformation that promotes binding of the antigen binding protein to the antigen. Examples of antigen binding proteins include a human antibody, a humanized antibody; a chimeric antibody; a recombinant antibody; a single chain antibody; a diabody; a triabody; a tetrabody; a Fab fragment; a F(ab')$_2$ fragment; an IgD antibody; an IgE antibody; an IgM antibody; an IgG1 antibody; an IgG2 antibody; an IgG3 antibody; or an IgG4 antibody, and fragments thereof. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, e.g., Korndorfer et al., 2003, *Proteins: Structure, Function, and Bioinformatics*, 53(1): 121-129 (2003); Roque et al., *Biotechnol. Prog.* 20:639-654 (2004). In addition, peptide antibody mimetics ("PAMs") can be used, as well as scaffolds based on antibody mimetics utilizing fibronectin components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain can be done in accordance with the definitions of Kabat et al. in Sequences of Proteins of Immunological Interest, $5^{th}$ Ed., US Dept. of Health and Human Services, PHS, NIH, NIH Publication no. 91-3242, (1991). As desired, the CDRs can also be redefined according an alternative nomenclature scheme, such as that of Chothia (see Chothia & Lesk, (1987) *J. Mol. Biol.* 196:901-917; Chothia et al., (1989) *Nature* 342:878-883 or Honegger & Pluckthun, (2001) *J. Mol. BioL* 309:657-670).

In the context of the instant disclosure an antigen binding protein is said to "specifically bind" or "selectively bind" its target antigen when the dissociation constant ($K_D$) is $\leq 10^{-8}$ M. The antibody specifically binds antigen with "high affinity" when the $K_D$ is $\leq 5 \times 10^{-9}$ M, and with "very high affinity" when the $K_D$ is $\leq 5 \times 10^{-10}$ M.

The term "antibody" includes reference to both glycosylated and non-glycosylated immunoglobulins of any isotype or subclass or to an antigen-binding region thereof that competes with the intact antibody for specific binding, unless otherwise specified. Additionally, the term "antibody" refers to an intact immunoglobulin or to an antigen binding portion thereof that competes with the intact antibody for specific binding, unless otherwise specified. Antigen binding portions can be produced by recombinant DNA techniques or by enzymatic or chemical cleavage of intact antibodies and can form an element of a protein of interest. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single aim of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, U.S. App. Pub. Nos. 05/0202512, 04/0202995, 04/0038291, 04/0009507, 03/0039958, Ward et al., (1989) *Nature* 341: 544-546).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., *Science* 242:423-26 (1988) and Huston et al., (1988) *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., (1993) *Proc. Natl. Acad. Sci. USA* 90:6444-48; and Poljak et al., (1994) *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

One or more CDRs can be incorporated into a molecule either covalently or noncovalently to make it an antigen binding protein. An antigen binding protein can incorporate the CDR(s) as part of a larger polypeptide chain, can covalently link the CDR(s) to another polypeptide chain, or can incorporate the CDR(s) noncovalently. The CDRs permit the antigen binding protein to specifically bind to a particular antigen of interest.

An antigen binding protein can have one or more binding sites. If there is more than one binding site, the binding sites can be identical to one another or can be different. For example, a naturally occurring human immunoglobulin typically has two identical binding sites, while a "bispecific" or "bifunctional" antibody has two different binding sites.

For purposes of clarity, and as described herein, it is noted that an antigen binding protein can, but need not, be of human origin (e.g., a human antibody), and in some cases will comprise a non-human protein, for example a rat or murine protein, and in other cases an antigen binding protein can comprise a hybrid of human and non-human proteins (e.g., a humanized antibody).

A protein of interest can comprise a human antibody. The term "human antibody" includes all antibodies that have one or more variable and constant regions derived from human immunoglobulin sequences. In one embodiment, all of the variable and constant domains are derived from human immunoglobulin sequences (a fully human antibody). Such antibodies can be prepared in a variety of ways, including through the immunization with an antigen of interest of a mouse that is genetically modified to express antibodies derived from human heavy and/or light chain-encoding genes, such as a mouse derived from a Xenomouse®, UltiMab™, or Velocimmune® system. Phage-based approaches can also be employed.

Alternatively, a protein of interest can comprise a humanized antibody. A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. Examples of how to make humanized antibodies can be found in U.S. Pat. Nos. 6,054,297, 5,886,152 and 5,877,293.

An "Fc" region, as the term is used herein, comprises two heavy chain fragments comprising the $C_H2$ and $C_H3$ domains of an antibody. The two heavy chain fragments are held together by two or more disulfide bonds and by hydrophobic interactions of the $C_H3$ domains. Proteins of interest comprising an Fc region, including antigen binding proteins and Fc fusion proteins, form another aspect of the instant disclosure.

A "hemibody" is an immunologically functional immunoglobulin construct comprising a complete heavy chain, a complete light chain and a second heavy chain Fc region paired with the Fc region of the complete heavy chain. A linker can, but need not, be employed to join the heavy chain Fc region and the second heavy chain Fc region. In particular embodiments a hemibody is a monovalent form of an antigen binding protein disclosed herein. In other embodiments, pairs of charged residues can be employed to associate one Fc region with the second Fc region. A hemibody can be a protein of interest in the context of the instant disclosure.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present. A cell culture can comprise one or more host cells.

The term "hybridoma" means a cell or progeny of a cell resulting from fusion of an immortalized cell and an antibody-producing cell. The resulting hybridoma is an immortalized cell that produces antibodies. The individual cells used to create the hybridoma can be from any mammalian source, including, but not limited to, hamster, rat, pig, rabbit, sheep, goat, and human. The term also encompasses trioma cell lines, which result when progeny of heterohybrid myeloma fusions, which are the product of a fusion between human cells and a murine myeloma cell line, are subsequently fused with a plasma cell. The term is meant to include any immortalized hybrid cell line that produces antibodies such as, for example, quadromas (see, e.g., Milstein et al., (1983) *Nature,* 537:3053).

The terms "culture" and "cell culture" are used interchangeably and refer to a cell population that is maintained in a medium under conditions suitable to survival and/or growth of the cell population. As will be clear to those of ordinary skill in the art, these terms also refer to the combination comprising the cell population and the medium in which the population is suspended.

The terms "polypeptide" and "protein" (e.g., as used in the context of a protein of interest or a polypeptide of interest) are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell, or polypeptides and proteins can be produced by a genetically-engineered or recombinant cell. Polypeptides and proteins can comprise molecules having the amino acid sequence of a native protein, or molecules having deletions from, additions to, and/or substitutions of one or more amino acids of the native sequence.

The terms "polypeptide" and "protein" encompass molecules comprising only naturally occurring amino acids, as well as molecules that comprise non-naturally occurring amino acids. Examples of non-naturally occurring amino acids (which can be substituted for any naturally-occurring amino acid found in any sequence disclosed herein, as desired) include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

A non-limiting list of examples of non-naturally occurring amino acids that can be inserted into a protein or polypeptide sequence or substituted for a wild-type residue in a protein or polypeptide sequence include β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl)alanine (2-Nal), 1,2,3,4-tetrahydroisoquinoline (Tic), 2-indanylglycine (Igl), para-iodophenylalanine (pI-Phe), para-aminophenylalanine (4AmP or 4-Amino-Phe), 4-guanidino phenylalanine (Guf), glycyllysinc (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), α,γ-diaminobutyric acid (Dab), diaminopropionic acid (Dap), cyclohexylalanine (Cha), 4-methyl-phenylalanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, can be used. In one embodiment 500 L to 2000 L bioreactors are used. In one embodiment, 1000 L to 2000 L bioreactors are used.

The term "cell culturing medium" (also called "culture medium," "cell culture media," "tissue culture media,") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

The nutrient solution may optionally be supplemented with additional optional components to optimize growth of cells, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal or plant protein (peptone or peptone mixtures, which can be obtained from animal byproducts, purified gelatin or plant material); antibiotics, e.g., gentamycin; cell protectants or surfactants such as Pluronic®F68 (also referred to as Lutrol® F68 and Kolliphor® P188; nonionic triblock copolymers composed of a central hydrophobic chain of polyoxypropylene (poly(propylene oxide)) flanked by two hydrophilic chains of polyoxyethylene (poly(ethylene oxide)); polyamines, e.g., putrescine, spermidine and spermine (see e.g., WIPO Publication No. WO 2008/154014) and pyruvate (see e.g. U.S. Pat. No. 8,053,238) depending on the requirements of the cells to be cultured and/or the desired cell culture parameters.

Cell culture media include those that are typically employed in and/or are known for use with any cell culture process, such as, but not limited to, batch, extended batch, fed-batch and/or perfusion or continuous culturing of cells.

A "base" (or batch) cell culture medium refers to a cell culture medium that is typically used to initiate a cell culture and is sufficiently complete to support the cell culture.

A "growth" cell culture medium refers to a cell culture medium that is typically used in cell cultures during a period of exponential growth, a "growth phase", and is sufficiently complete to support the cell culture during this phase. A growth cell culture medium may also contain selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone.

A "production" cell culture medium refers to a cell culture medium that is typically used in cell cultures during the transition when exponential growth is ending and protein production takes over, "transition" and/or "product" phases, and is sufficiently complete to maintain a desired cell density, viability and/or product titer during this phase.

A "perfusion" cell culture medium refers to a cell culture medium that is typically used in cell cultures that are maintained by perfusion or continuous culture methods and is sufficiently complete to support the cell culture during this process. Perfusion cell culture medium formulations may be richer or more concentrated than base cell culture medium formulations to accommodate the method used to remove the spent medium. Perfusion cell culture medium can be used during both the growth and production phases.

Concentrated cell culture medium can contain some or all of the nutrients necessary to maintain the cell culture; in particular, concentrated medium can contain nutrients identified as or known to be consumed during the course of the production phase of the cell culture. Concentrated medium may be based on just about any cell culture media formulation. Such a concentrated feed medium can contain some or all the components of the cell culture medium at, for example, about 2×, 3×, 4×, 5×, 6×, 7×, 8×, 9×, 10×, 12×, 14×, 16×, 20×, 30×, 50×, 100×, 200×, 400×, 600×, 800×, or even about 1000× of their normal amount.

The components used to prepare cell culture medium may be completely milled into a powder medium formulation; partially milled with liquid supplements added to the cell culture medium as needed; or added in a completely liquid form to the cell culture.

Cell cultures can also be supplemented with independent concentrated feeds of particular nutrients which may be difficult to formulate or are quickly depleted in cell cultures. Such nutrients may be amino acids such as tyrosine, cysteine and/or cystine (see e.g., WIPO Publication No. 2012/145682). In one embodiment, a concentrated solution of tyrosine is independently fed to a cell culture grown in a cell culture medium containing tyrosine, such that the concentration of tyrosine in the cell culture does not exceed 8 mM. In another embodiment, a concentrated solution of tyrosine and cystine is independently fed to the cell culture being grown in a cell culture medium lacking tyrosine, cystine or cysteine. The independent feeds can begin prior to or at the start of the production phase. The independent feeds can be accomplished by fed batch to the cell culture medium on the same or different days as the concentrated feed medium. The independent feeds can also be perfused on the same or different days as the perfused medium.

"Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

The term "bioreactor" means any vessel useful for the growth of a cell culture. The cell cultures of the instant disclosure can be grown in a bioreactor, which can be selected based on the application of a protein of interest that is produced by cells growing in the bioreactor. A bioreactor can be of any size so long as it is useful for the culturing of cells; typically, a bioreactor is sized appropriate to the volume of cell culture being grown inside of it. Typically, a bioreactor will be at least 1 liter and may be 2, 5, 10, 50, 100, 200, 250, 500, 1,000, 1500, 2000, 2,500, 5,000, 8,000, 10,000, 12,000 liters or more, or any volume in between. The internal conditions of the bioreactor, including, but not limited to pH and temperature, can be controlled during the culturing period. Those of ordinary skill in the art will be aware of, and will be able to select, suitable bioreactors for use in practicing the present invention based on the relevant considerations.

"Cell density" refers to the number of cells in a given volume of culture medium. "Viable cell density" refers to the number of live cells in a given volume of culture medium, as determined by standard viability assays (such as trypan blue dye exclusion method).

The term "cell viability" means the ability of cells in culture to survive under a given set of culture conditions or experimental variations. The term also refers to that portion of cells which are alive at a particular time in relation to the total number of cells, living and dead, in the culture at that time.

"Packed cell volume" (PCV), also referred to as "percent packed cell volume" (% PCV), is the ratio of the volume occupied by the cells, to the total volume of cell culture, expressed as a percentage (see Stettler, et al., (2006) Biotechnol Bioeng. December 20:95(6):1228-33). Packed cell volume is a function of cell density and cell diameter; increases in packed cell volume could arise from increases in either cell density or cell diameter or both. Packed cell volume is a measure of the solid content in the cell culture. Solids are removed during harvest and downstream purification. More solids mean more effort to separate the solid material from the desired product during harvest and downstream purification steps. Also, the desired product can become trapped in the solids and lost during the harvest process, resulting in a decreased product yield. Since host cells vary in size and cell cultures also contain dead and dying cells and other cellular debris, packed cell volume is a more accurate way to describe the solid content within a cell culture than cell density or viable cell density. For example, a 2000 L culture having a cell density of $50 \times 10^6$ cells/ml would have vastly different packed cell volumes depending on the size of the cells. In addition, some cells, when in a growth-arrested state, will increase in size, so the packed cell volume prior to growth-arrest and post growth-arrest will likely be different, due to increase in biomass as a result to cell size increase.

"Growth-arrest", which may also be referred to as "cell growth-arrest", is the point where cells stop increasing in number or when the cell cycle no longer progresses. Growth-arrest can be monitored by determining the viable cell density of a cell culture. Some cells in a growth-arrested state may increase in size but not number, so the packed cell volume of a growth-arrested culture may increase. Growth-arrest can be reversed to some extent, if the cells are not in declining health, by reversing the conditions that lead to growth arrest.

The term "titer" means the total amount of a polypeptide or protein of interest (which may be a naturally occurring or recombinant protein of interest) produced by a cell culture in a given amount of medium volume. Titer can be expressed in units of milligrams or micrograms of polypeptide or protein per milliliter (or other measure of volume) of medium. "Cumulative titer" is the titer produced by the cells during the course of the culture, and can be determined, for example, by measuring daily titers and using those values to calculate the cumulative titer.

The term "fed-batch culture" refers to a form of suspension culture and means a method of culturing cells in which additional components are provided to the culture at a time or times subsequent to the beginning of the culture process. The provided components typically comprise nutritional supplements for the cells which have been depleted during the culturing process. Additionally or alternatively, the additional components may include supplementary components (e.g., a cell-cycle inhibitory compound). A fed-batch culture is typically stopped at some point and the cells and/or components in the medium are harvested and optionally purified.

The terms "integrated viable cell density" or "IVCD" are used interchangeably and mean the average density of viable cells over the course of the culture multiplied by the amount of time the culture has run.

"Cumulative viable cell density" (CVCD) is calculated by multiplying an average viable cell density (VCD) between two time-points with the time duration between those two time points. CVCD is the area under the curve formed by plotting the VCD versus time.

Description of Cell Culture Process

During recombinant protein production it is desirable to have a controlled system where cells are grown to a desired density and then the physiological state of the cells is switched to a growth-arrested, high productivity state where the cells use energy and substrates to produce the recombinant protein of interest instead of making more cells. Various methods for accomplishing this goal exist, and include temperature shifts and amino acid starvation, as wells as use of a cell-cycle inhibitor or other molecule that can arrest cell growth without causing cell death.

The production of a recombinant protein begins with establishing a mammalian cell production culture of cells that express the protein, in a culture plate, flask, tube, bioreactor or other suitable vessel. Smaller production bioreactors are typically used, in one embodiment the bioreactors are 500 L to 2000 L. In another embodiment, 1000 L-2000 L bioreactors are used. The seed cell density used to inoculate the bioreactor can have a positive impact on the level of recombinant protein produced. In one embodiment the bioreactor is inoculated with at least $0.5 \times 10^6$ up to and beyond $3.0 \times 10^6$ viable cells/mL in a serum-free culture medium. In another embodiment the inoculation is $1.0 \times 10^6$ viable cells/mL.

The mammalian cells then undergo an exponential growth phase. The cell culture can be maintained without supplemental feeding until a desired cell density is achieved. In one embodiment the cell culture is maintained for up to three days with or without supplemental feeding. In another embodiment the culture can be inoculated at a desired cell density to begin the production phase without a brief growth phase. In any of the embodiments herein the switch from the growth phase to production phase can also be initiated by any of the afore-mentioned methods.

At the transition between the growth phase and the production phase, and during the production phase, the percent packed cell volume (% PCV) is equal to or less than 35%. The desired packed cell volume maintained during the production phase is equal to or less than 35%. In one embodiment the packed cell volume is equal to or less than 30%. In another embodiment the packed cell volume is equal to or less than 20%. In yet another embodiment the packed cell volume is equal to or less than 15%. In a further embodiment the packed cell volume is equal to or less than 10%.

The desired viable cell density at the transition between the growth and production phases and maintained during the production phase van be various depending on the projects. It can be decided based on the equivalent packed cell volume from the historical data. In one embodiment, the viable cell density is at least about $10\times10^6$ viable cells/mL to $80\times10^6$ viable cells/mL. In one embodiment the viable cell density is at least about $10\times10^6$ viable cells/mL to $70\times10^6$ viable cells/mL. In one embodiment the viable cell density is at least about $10\times10^6$ viable cells/mL to $60\times10^6$ viable cells/mL. In one embodiment the viable cell density is at least about $10\times10^6$ viable cells/mL to $50\times10^6$ viable cells/mL. In one embodiment the viable cell density is at least about $10\times10^6$ viable cells/mL to $40\times10^6$ viable cells/mL. In another embodiment the viable cell density is at least about $10\times10^6$ viable cells/mL to $30\times10^6$ viable cells/mL. In another embodiment the viable cell density is at least about $10\times10^6$ viable cells/mL to $20\times10^6$ viable cells/mL. In another embodiment, the viable cell density is at least about $20\times10^6$ viable cells/mL to $30\times10^6$ viable cells/mL. In another embodiment the viable cell density is at least about $20\times10^6$ viable cells/mL to at least about $25\times10^6$ viable cells/mL, or at least about $20\times10^6$ viable cells/mL.

Lower packed cell volume during the production phase helps mitigate dissolved oxygen sparging problems that can hinder higher cell density perfusion cultures. The lower packed cell volume also allows for a smaller media volume which allows for the use of smaller media storage vessels and can be combined with slower flow rates. Lower packed cell volume also has less impact on harvest and downstream processing, compared to higher cell biomass cultures. All of which reduces the costs associated with manufacturing recombinant protein therapeutics.

Three methods are typically used in commercial processes for the production of recombinant proteins by mammalian cell culture: batch culture, fed-batch culture, and perfusion culture. Batch culture is a discontinuous method where cells are grown in a fixed volume of culture media for a short period of time followed by a full harvest. Cultures grown using the batch method experience an increase in cell density until a maximum cell density is reached, followed by a decline in viable cell density as the media components are consumed and levels of metabolic by-products (such as lactate and ammonia) accumulate. Harvest typically occurs at the point when the maximum cell density is achieved (typically $5\text{-}10\times10^6$ cells/mL, depending on media formulation, cell line, etc). The batch process is the simplest culture method, however viable cell density is limited by the nutrient availability and once the cells are at maximum density, the culture declines and production decreases. There is no ability to extend a production phase because the accumulation of waste products and nutrient depletion rapidly lead to culture decline, (typically around 3 to 7 days).

Fed-batch culture improves on the batch process by providing bolus or continuous media feeds to replenish those media components that have been consumed. Since fed-batch cultures receive additional nutrients throughout the run, they have the potential to achieve higher cell densities (>10 to $30\times10^6$ cells/ml, depending on media formulation, cell line, etc)) and increased product titers, when compared to the batch method. Unlike the batch process, a biphasic culture can be created and sustained by manipulating feeding strategies and media formulations to distinguish the period of cell proliferation to achieve a desired cell density (the growth phase) from the period of suspended or slow cell growth (the production phase). As such, fed batch cultures have the potential to achieve higher product titers compared to batch cultures. Typically a batch method is used during the growth phase and a fed-batch method used during the production phase, but a fed-batch feeding strategy can be used throughout the entire process. However, unlike the batch process, bioreactor volume is a limiting factor which limits the amount of feed. Also, as with the batch method, metabolic by-product accumulation will lead to culture decline, which limits the duration of the production phase, about 1.5 to 3 weeks. Fed-batch cultures are discontinuous and harvest typically occurs when metabolic by-product levels or culture viability reach predetermined levels. When compared to a batch culture, in which no feeding occurs, a fed batch culture can produce greater amounts of recombinant protein. See e.g. U.S. Pat. No. 5,672,502.

Perfusion methods offer potential improvement over the batch and fed-batch methods by adding fresh media and simultaneously removing spent media. Typical large scale commercial cell culture strategies strive to reach high cell densities, $60\text{-}90(+)\times10^6$ cells/mL where almost a third to over one-half of the reactor volume is biomass. With perfusion culture, extreme cell densities of $>1\times10^8$ cells/mL have been achieved and even higher densities arc predicted. Typical perfusion cultures begin with a batch culture start-up lasting for a day or two followed by continuous, step-wise and/or intermittent addition of fresh feed media to the culture and simultaneous removal of spent media with the retention of cells and additional high molecular weight compounds such as proteins (based on the filter molecular weight cutoff) throughout the growth and production phases of the culture. Various methods, such as sedimentation, centrifugation, or filtration, can be used to remove spent media, while maintaining cell density. Perfusion flow rates of a fraction of a working volume per day up to many multiple working volumes per day have been reported.

An advantage of the perfusion process is that the production culture can be maintained for longer periods than batch or fed-batch culture methods. However, increased media preparation, use, storage and disposal are necessary to support a long term perfusion culture, particularly those with high cell densities, which also need even more nutrients, and all of this drives the production costs even higher, compared to batch and fed batch methods. In addition, higher cell densities can cause problems during production, such as maintaining dissolved oxygen levels and problems with increased gassing including supplying more oxygen and removing more carbon dioxide, which would result in more foaming and the need for alterations to antifoam strategies; as well as during harvest and downstream processing where the efforts required to remove the excessive cell material can result in loss of product, negating the benefit of increased titer due to increased cell mass.

Also provided is a large scale cell culture strategy that combines fed batch feeding during the growth phase followed by continuous perfusion during the production phase. The method targets a production phase where the cell culture is maintained at a packed cell volume of less than or equal to 35%.

In one embodiment, a fed-batch culture with bolus feeds is used to maintain a cell culture during the growth phase. Perfusion feeding can then be used during a production phase. In one embodiment, perfusion begins when the cells have reached a production phase. In another embodiment, perfusion begins on or about day 3 to on or about day 9 of the cell culture. In another embodiment perfusion begins on or about day 5 to on or about day 7 of the cell culture.

Using bolus feeding during the growth phase allows the cells to transition into the production phase, resulting in less dependence on a temperature shift as a means of initiating and controlling the production phase, however a temperature shift of 36° C. to 31° C. can take place between the growth phase and production phase. In one embodiment the shift is from 36° C. to 33° C. In another embodiment the initiation of cell growth-arrest in the fed-batch culture can be initiated by exposing the fed-batch culture to a cell-cycle inhibitor. In another embodiment the initiation of cell growth-arrest in the fed-batch culture can be achieved by perfusion with a serum free perfusion medium comprising a cell-cycle inhibitor.

As described herein, the bioreactor can be inoculated with at least $0.5 \times 10^6$ up to and beyond $3.0 \times 10^6$ viable cells/mL in a serum-free culture medium, for example $1.0 \times 106$ viable cells/mL.

Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. The cells are retained in the culture and the spent medium that is removed is substantially free of cells or has significantly fewer cells than the culture. Recombinant proteins expressed by the cell culture can also be retained in the culture. Perfusion can be accomplished by a number of means including centrifugation, sedimentation, or filtration, See e.g. Voisard et al., (2003), Biotechnology and Bioengineering 82:751-65. An example of a filtration method is alternating tangential flow filtration. Alternating tangential flow is maintained by pumping medium through hollow-fiber filter modules. See e.g. U.S. Pat. No. 6,544,424; Furey (2002) Gen. Eng. News. 22 (7), 62-63.

"Perfusion flow rate" is the amount of media that is passed through (added and removed) from a bioreactor, typically expressed as some portion or multiple of the working volume, in a given time. "Working volume" refers to the amount of bioreactor volume used for cell culture. In one embodiment the perfusion flow rate is one working volume or less per day. Perfusion feed medium can be formulated to maximize perfusion nutrient concentration to minimize perfusion rate.

Cell cultures can be supplemented with concentrated feed medium containing components, such as nutrients and amino acids, which are consumed during the course of the production phase of the cell culture. Concentrated feed medium may be based on just about any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount. Concentrated feed media are often used in fed batch culture processes.

The method according to the present invention may be used to improve the production of recombinant proteins in multiple phase culture processes. In a multiple stage process, cells are cultured in two or more distinct phases. For example cells may be cultured first in one or more growth phases, under environmental conditions that maximize cell proliferation and viability, then transferred to a production phase, under conditions that maximize protein production.

In a commercial process for production of a protein by mammalian cells, there are commonly multiple, for example, at least about 2, 3, 4, 5, 6, 7, 8, 9, or 10 growth phases that occur in different culture vessels preceding a final production culture.

The growth and production phases may be preceded by, or separated by, one or more transition phases. In multiple phase processes, the method according to the present invention can be employed at least during the growth and production phase of the final production phase of a commercial cell culture, although it may also be employed in a preceding growth phase. A production phase can be conducted at large scale. A large scale process can be conducted in a volume of at least about 100, 500, 1000, 2000, 3000, 5000, 7000, 8000, 10,000, 15,000, 20,000 liters. In one embodiment production is conducted in 500 L, 1000 L and/or 2000 L bioreactors.

A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift. The cell cultures can be maintained for days or even weeks while the cells produce the desired protein(s).

Samples from the cell culture can be monitored and evaluated using any of the analytical techniques known in the art. A variety of parameters including recombinant protein and medium quality and characteristics can be monitored for the duration of the culture. Samples can be taken and monitored intermittently at a desirable frequency, including continuous monitoring, real time or near real time.

Typically the cell cultures that precede the final production culture (N–x to N–1) are used to generate the seed cells that will be used to inoculate the production bioreactor, the N–1 culture. The seed cell density can have a positive impact on the level of recombinant protein produced. Product levels tend to increase with increasing seed density. Improvement in titer is tied not only to higher seed density, but is likely to be influenced by the metabolic and cell cycle state of the cells that are placed into production.

Seed cells can be produced by any culture method. One such method is a perfusion culture using alternating tangential flow filtration. An N–1 bioreactor can be run using alternating tangential flow filtration to provide cells at high density to inoculate a production bioreactor. The N–1 stage may be used to grow cells to densities of $>90 \times 10^6$ cells/mL. The N–1 bioreactor can be used to generate bolus seed cultures or can be used as a rolling seed stock culture that could be maintained to seed multiple production bioreactors at high seed cell density. The duration of the growth stage of production can range from 7 to 14 days and can be designed so as to maintain cells in exponential growth prior to inoculation of the production bioreactor. Perfusion rates, medium formulation and timing are optimized to grow cells and deliver them to the production bioreactor in a state that is most conducive to optimizing their production. Seed cell densities of $>15 \times 10^6$ cells/mL can be achieved for seeding production bioreactors. Higher seed cell densities at inoculation can decrease or even eliminate the time needed to reach a desired production density.

The invention finds particular utility in regulating the presence and/or amount of glycosylation of a recombinant protein. The cell lines (also referred to as "host cells") used in the invention are genetically engineered to express a polypeptide of commercial or scientific interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture*, 1990, pp. 15-69.

Animal cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NSO, NS1), PC12, WI38 cells, and Chinese hamster ovary (CHO) cells. CHO cells are widely used for the production of complex recombinant proteins, e.g. cytokines, clotting factors, and antibodies (Brasel et al. (1996), *Blood* 88:2004-2012; Kaufman et al. (1988), *J. Biol Chem* 263: 6352-6362; McKinnon et al. (1991), *J Mol Endocrinol* 6:231-239; Wood et al. (1990), *J. Immunol*. 145:3011-3016). The dihydrofolate reductase (DHFR)-deficient mutant cell lines (Urlaub et al. (1980), *Proc Natl Acad Sci USA* 77: 4216-4220), DX1311 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

In another aspect, the present invention provides host cells into which a recombinant expression vector has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. Numerous transfection methods are known in the art, and include the use of lipids (for example, Lipofectamin®), calcium phosphate, cationic polymers, DEAE-dextran, activated dendrimers and magnetic beads. Additional transfection methods utilize instrument-based techniques. Examples include electroporation, biolistic technology, microinjection, and laserfection/optoinjection, which uses light (for instance, a laser) to introduce nucleic acid into a host cell.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Proteins of Interest

The methods of the invention can be used to culture cells that express recombinant proteins of interest. The expressed recombinant proteins may be secreted into the culture medium from which they can be recovered and/or collected. In addition, the proteins can be purified, or partially purified, from such culture or component (e.g., from culture medium) using known processes and products available from commercial vendors. The purified proteins can then be "formulated", meaning buffer exchanged, sterilized, bulk-packaged, and/or packaged for a final user. Suitable formulations for pharmaceutical compositions include those described in *Remington's Pharmaceutical Sciences*, 18th ed. 1995, Mack Publishing Company, Easton, Pa.

Examples of polypeptides that can be produced with the methods of the invention include proteins comprising amino acid sequences identical to or substantially similar to all or part of one of the following proteins: tumor necrosis factor (TNF), flt3 ligand (WO 94/28391), erythropoietin, thrombopoeitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be produced according to the inventive methods may be found in, for example, *Human Cytokines: Handbook for Basic and Clinical Research*, all volumes (Aggarwal and Gutterman, eds. Blackwell Sciences, Cambridge, Mass., 1998); *Growth Factors: A Practical Approach* (McKay and Leigh, eds., Oxford University Press inc., New York, 1993); and *The Cytokine Handbook*, Vols. 1 and 2 (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064,), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

Examples of antibodies that can be produced include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-1 receptor, IL-2 receptor, IL-4 receptor, IL-6 receptor, IL-13 receptor, IL-1 8 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, integrins (including integrins comprising alpha4beta7), TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mulans*, and *Staphlycoccus aureus*.

Specific examples of known antibodies which can be produced using the methods of the invention include but are not limited to adalimumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, eculizumab, etrolizumab, evolocumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizomab, zalutumumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05; Harbury et al. (1994), *Nature* 371:80-83; Hakansson et al.(1999), *Structure* 7:255-64. Specifically included among such recombinant fusion proteins are proteins in which a portion of a receptor is fused to an Fc portion of an antibody such as etanercept (a p75 TNFR:Fc), abatacept and belatacept (CTLA4:Fc).

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

A monoclonal antibody producing Chinese hamster ovary (CHO) cell line expressing a recombinant human antibody that historically exhibited low levels of high-mannose (HM) expression (MAb A) was used for siRNA experiments. The cell line was clonally derived using DHFR based selection;

for routine culture, cells were cultivated in suspension, in selective medium containing methotrexate (MTX). Cultures were maintained in either vented 125 mL or 250 mL Erlenmeyer shake flasks (Corning Life Sciences, Lowell, Mass.) or 50 mL vented spin tubes (TPP, Trasadingen, Switzerland) at 36° C., 5% $CO_2$ and 85% relative humidity. Erlenmeyer flasks were shaken at 120 rpm with a 25 mm orbital diameter in a large-capacity automatic $CO_2$ incubator (Thermo Fisher Scientific, Waltham, Mass.) and spin tubes were shaken at 225 rpm, 50 mm orbital diameter in a large capacity ISF4-X incubator (Kuhner AG, Basel, Switzerland).

Eight different 19mer siRNAs were tested for Mgat1, Mgat2 and Slc35a2. siRNAs were transiently transfected into the MAb A cell line using Lipofectamine® RNAiMAX (Invitrogen; Life Technologies; a lipid-based transfection reagent that complexes with nucleic acids and facilitates transfection of cells with the nucleic acid) according to the manufacturer's protocol. Briefly, cells were plated at $2 \times 10^5$ per well onto six-well plates (Corning) with 500 microL media on the day of transfection. For transfection 10 pmol of siRNA was complexed to 1.5 microL of Lipofectamine RNAiMAX in 100microL Opti-Mem I medium and incubated for 10 minutes at room temperature. The RNAi-Lipofectamine RNAiMax reagent complex was then added to each well. The plate was incubated for 3 days at 36° C. in $CO_2$ incubator. Cells were lysed using 1× lysis buffer (Affymetrix Inc., Sanata Clara, Calif.) at 50° C. for 1 hour. The lysates were used for mRNA expression analysis by QuantiGene® multiplex assay using FLEXMAP 3D® system (Luminex, Austin Tex.; a protein and genomic multiplex bead array assay).

For mRNA expression analysis, QuantiGene Plex 2.0 Reagent System (Affymetrix Inc., Santa Clara, Calif.) was utilized. Briefly, cell pellets from $5 \times 10^5$ viable cells were lysed using 1× lysis buffer (QS0100) (Affymetrix Inc., Santa Clara, Calif.) supplemented with proteinase K (stock concentration 50 mg/mL), and incubated at 50° C. for 1 hour. Cell lysates were stored at −80° C. until ready for use. A customized gene specific probe set targeting Mgat1, Mgat2, and Slc35a3, as well as normalization genes, was used (Affymetrix, Inc. Santa Clara, Calif.). Frozen lysates were thawed and processed using the standard Affymetrix protocol for mRNA expression level analysis.

Data were derived from measuring the median reporter fluorescence from 100 beads per gene per well assayed and represented as median fluorescence intensity (MFI). Background signals were determined in the absence of target mRNAs from the blank sample and were subtracted from signals obtained in the presence of target mRNAs. Fluorescent intensity of the gene of interest was normalized to the two housekeeping genes: GusB and TBP.

$$\text{Norm Ratio} = \frac{\text{MFI of the gene of interest}}{\text{MFI of housekeeping genes}}$$

The sensitivity of the assay for each target RNA was evaluated by determining the limit of detection (LOD), defined as the target concentration at which the signal is three standard deviations above the background. The Coefficient of Variation (CV) measures the assay precision and is a ratio of standard deviation and average.

All the samples were run in triplicate and lysis buffer was used as blank. Samples were analyzed using Bio-Plex 3D plate reader (Luminex Corporation) and data acquired using Bio-Plex Data Manager 5.0 software (Bio-Rad Laboratories, Hercules, Calif.).

For each gene, two siRNAs were selected that achieved a >85% knockdown without any significant off target effects. The selected siRNAs were then transfected into the MAb A cell line and a 10 day fed-batch antibody production run was performed. In fed-batch production studies cells were seeded at $3.5 \times 10^5$ cells/mL into production media. A three mL working volume was used in 24 deep well plates (Axygen Scientific, Union City, Calif.), or a 25 mL working volume in 125 mL vented shaker flasks. Cultures were fed a single bolus feed of 7% of the initial culture volume on days 3, 6, and 8. Glucose was fed to a 10 g/L target on days 3, 6 and 8. Centrifuged conditioned media was harvested on day 10 of the production run. Samples were also taken on days 3, 6, 8 and 10 for growth, viability and metabolic data and on days 6, 8 and 10 for titer and HM analysis.

Cell pellet samples were taken from cultures on days 3, 6, 8, and 10 for mRNA expression analysis; results are shown in Table 1 below.

TABLE 1

Reduction in Levels of Mgat1, Mgat2 and Slc35a2 by siRNA Treatment

| | % Knockdown | | | |
|---|---|---|---|---|
| Samples | Day 3 | Day 6 | Day D8 | Day 10 |
| si RNA-Mgat1 | 90 | 83 | 85 | 67 |
| si RNA-Mgat2 | 78 | 64 | 71 | 59 |
| si RNA-SLC35A2 | 57 | 51 | 14 | 7 |

The mRNA expression analysis showed that Mgat1 and Mgat2 transcript levels were reduced by >50% over the 10 day production run. The expression levels of Slc35a2 were reduced by >50% from days 3 to 6, however by days 8 and 10 only a 7-14% reduction was seen.

Antibody titer and %HM were determined on day ten of the fed-batch. Titers were measured by affinity protein A POROS PA ID Sensor Cartridge by using Waters UPLC. High mannose content was measured using a Caliper GX II HM assay (Caliper Life Sciences Inc., a PerkinElmer company) or using UPLC HILIC (Hydrophilic Interaction Chromotography) (Waters Acquity UPLC equipped with an UPLC Fluorescence (FLR) detector used with Acquity UPLC BEH Glycan Column). Results are shown in Table 2 below (results presented as average value plus/minus the standard deviation).

TABLE 2

Titer and % HM of Cell Lines Treated with siRNA

| samples | Titer (g/L) | % HM |
|---|---|---|
| No siRNA | 0.75 ± 0.09 | 0.81 ± 0.07 |
| siRNA MGAT1 | 0.73 ± 0.05 | 72.42 ± 3.28 |
| siRNA MGAT2 | 0.87 ± 0.27 | 1.98 ± 0.31 |
| siRNA Slc35a2 | 0.57 ± 0.36 | 1.56 ± 0.29 |

Analysis of these results indicated that in cells treated with the Mgat1 siRNA, levels of HM were increased by 70% whereas knockdown of either Mgat2 or Slc35a2 did not significantly impact HM. However, by day 10, the levels of Slc35a2 had recovered to 90% of control values, so it is not possible to rule out a role for this gene in modulating HM for this experiment. No significant changes in titer of antibody produced were observed with siRNA treatment. Furthermore, siRNA treatment did not appear to impact productivity or cell viability, indicating that the increased HM levels observed with reduced Mgat1 mRNA expression was likely to be directly related to decreased Mgat1 activity.

Example 2

A monoclonal antibody producing Chinese hamster ovary (CHO) cell line expressing a recombinant human antibody that historically exhibited high levels (i.e., >10%) of high-mannose-type glycans (MAb B) was used for transfection experiments. The cell line was clonally derived using DHFR based selection; for routine culture, cells were cultivated in suspension, in selective medium containing MTX. Cultures were maintained in either vented 125 mL or 250 mL Erlenmeyer shake flasks (Corning Life Sciences, Lowell, Mass.) or 50 mL vented spin tubes (TPP, Trasadingen, Switzerland) substantially as previously described.

MAb B cells were transfected with either: a null expression vector control, a bicistronic expression vector containing Mgat1 and Mgat2 linked with furin pep2A (M1M2), a vector containing Slc35a2 (S) or a co-transfection of the Mgat1, Mgat2 and Slc35a2 vectors (M1M2S). After recovery of these cells to greater than 80% viability in selective medium they were single cell cloned using flow cytometry. For those cell lines which were derived from a single cell, the expression levels of the genes of interest were analyzed. For each of the four different vector configurations greater than 40 clones were analyzed for expression of the genes of interest and based on this analysis twenty overexpressing cell lines and ten control cell lines were chosen for further characterization in two separate 10 day fed-batch production runs, performed substantially as described previously.

Figure 2:
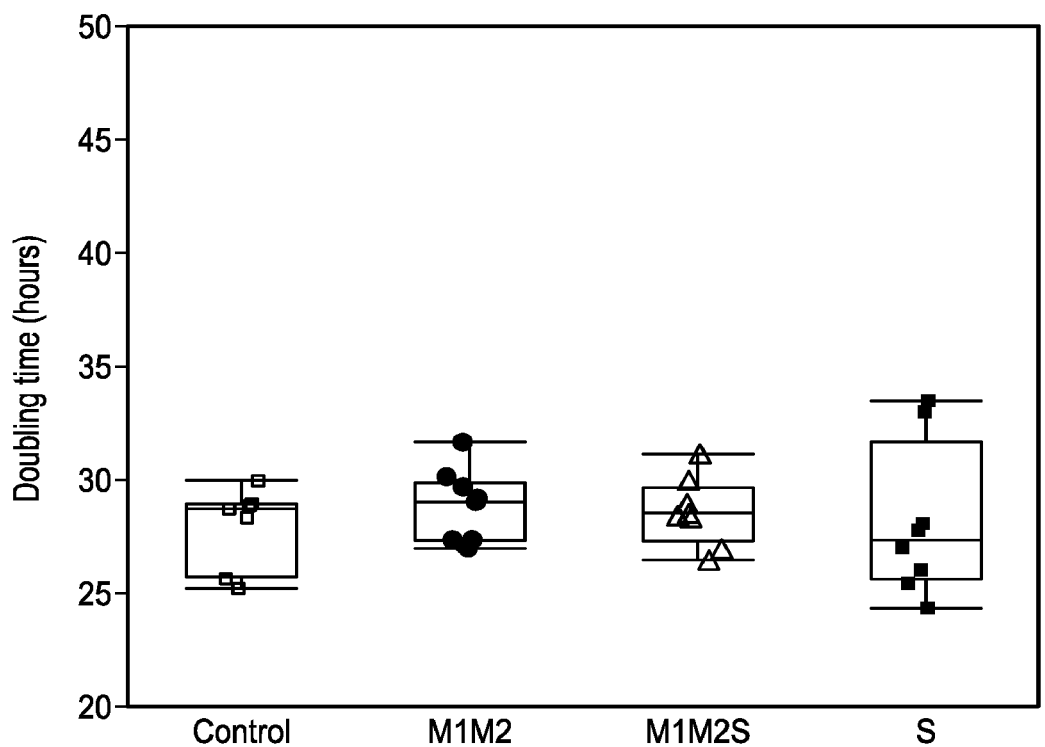
FIG. 2 illustrates clonal variability in doubling time during passaging for the cell lines used for the second set of fed-batch cells in Example 2. In this Example, cells from a cell line expressing MAb B were transformed to overexpress Mgat1, Mgat2 and/or Slc35A2. M1M2 designates cell lines overexpressing Mgat1 & Mgat2; M1M2S designates cell lines overexpressing Mgat1, Mgat2 and Slc35a2; and S designates cell lines overexpressing Slc35A2. Control cells were transformed with empty vector. Individual clones are designated as described for FIG. 1; the parameters for each box are the same as described for FIG. 1.

At the start of the first fed-batch production, on average the doubling time for the overexpressing cell lines was higher (>25 hours) and PDL were lower as compared to the control (<25 hours) with higher PDL (FIG. 1). Therefore the second 10 day fed-batch experiment was performed for a smaller subset of clones which all exhibited similar doubling times (FIG. 2).

Statistical analysis of mRNA expression in the selected clones from the second fed-batch experiment confirmed that the fold change in overexpression was significant as compared to the control. The Mgat2 gene had a greater fold increase in expression as compared to the Mgat1 gene. Results are shown in Table 3 below.

TABLE 3

Average fold increase in the transcript levels of the Mgat1, Mgat2 and Slc35a2 for three sets of overexpressed clones.

| Samples | Mgat1 | Mgat2 | Slc35A2 |
|---|---|---|---|
| M1M2 | 6.24 | 26.29 | 0.99 |
| M1M2S | 1.45 | 7.76 | 37.28 |
| S | 0.83 | 0.99 | 27.1 |

To further investigate the levels of overexpression induced, the protein levels of Mgat1 and Mgat2 were quantified using liquid chromatography-tandem mass spectrometry (LC-MS/MS). A control cell line that was transfected with the empty vector (EV) as well as two lines overexpressing both Mgat1 and Mgat2 (B1 and B2) were analyzed. Results are shown in Table 4 below. The relative protein expression is measured in parts per million (ppm).

TABLE 4

Normalized mRNA and Protein levels in a control cell line and two cell lines overexpressing Mgat1 and Mgat2 at Day 10

| | Proteins | EV | B1 | B2 |
|---|---|---|---|---|
| mRNA | Mgat1 | 0.527 | 5.855 | 13.042 |
| | Mgat2 | 1.242 | 20.313 | 44.156 |
| | Mgat2/Mgat1 | 2.4 | 3.5 | 3.4 |
| Protein | MGAT1 (ppm) | 0.8 | 101 | 160.1 |
| | MGAT2 (ppm) | 6.6 | 527.8 | 783.4 |
| | MGAT2/MGAT1 | 8.3 | 5.2 | 4.9 |

As Table 4 demonstrates, EV exhibited basal expression levels of Mgat1 and Mgat2, while the expression levels of these proteins were significantly increased in the B1 and B2 cell lines. Furthermore, in the B1 and B2 cell lines, Mgat2 displayed elevated expression levels compared to Mgat1. These data correlate well to those observed for the mRNA expression levels of Mgat1 and Mgat2 in day 10.

In contrast, the expression levels of housekeeping control protein (GAPDH; data not shown) remained constant for these three cell lines on days 8 and 10 (the two days on which protein expression were analyzed).

Figure 3:
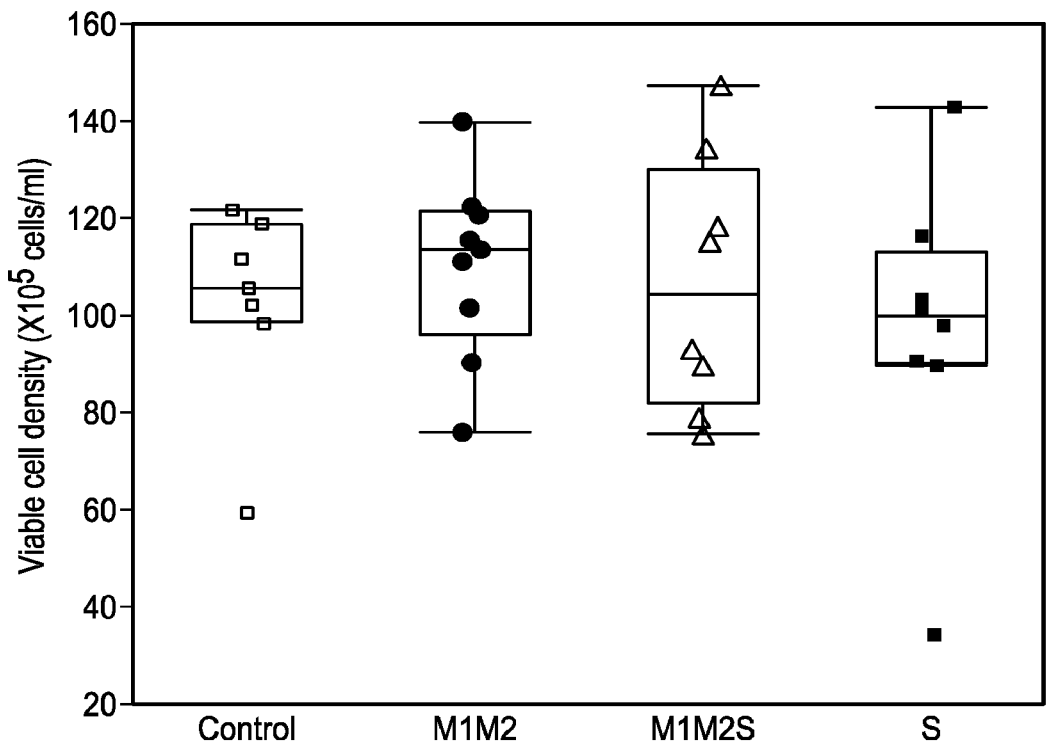
FIG. 3 presents the growth shown in terms of viable cell density is comparable for all the overexpressed cell lines (M1M2, M1M2S and S) as compared to control on day 10 of the second fed-batch experiment described in Example 2. The individual values in each box again illustrate the clonal variability observed. Individual clones are designated as described for FIG. 1; the parameters for each box are the same as described for FIG. 1.
Figure 4:
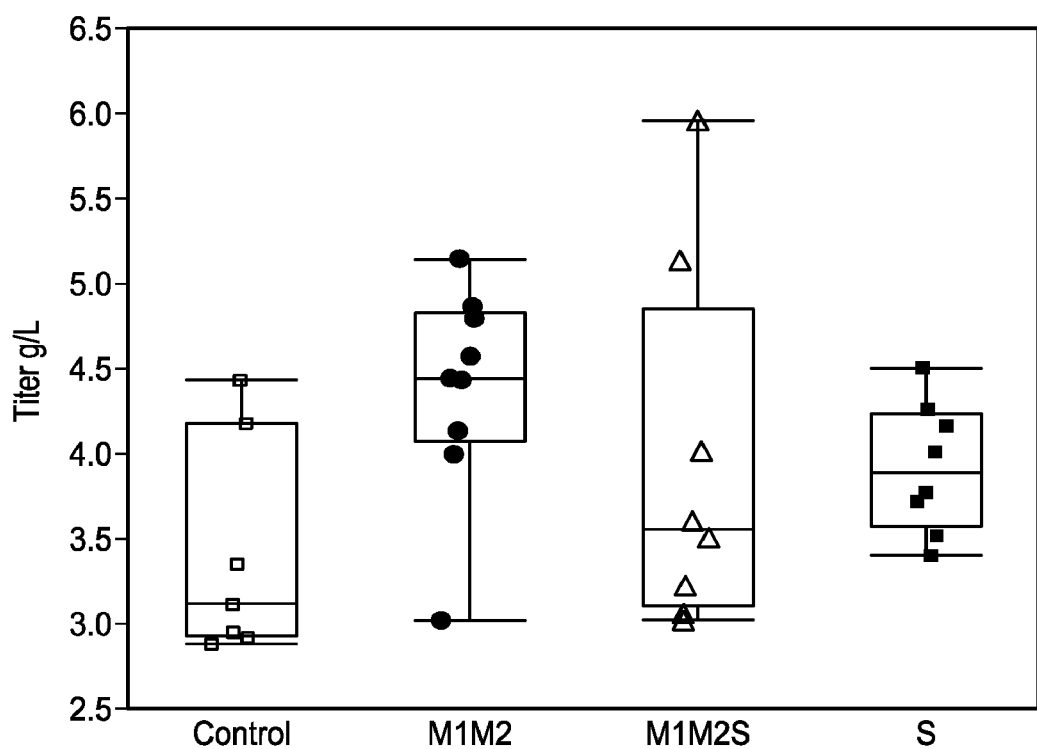
FIG. 4 presents a comparison of the clonal variability in titer of antibody produced during the second fed-batch experiment described in Example 2. Individual clones are designated as described for FIG. 1; the parameters for each box are the same as described for FIG. 1.
Figure 5:
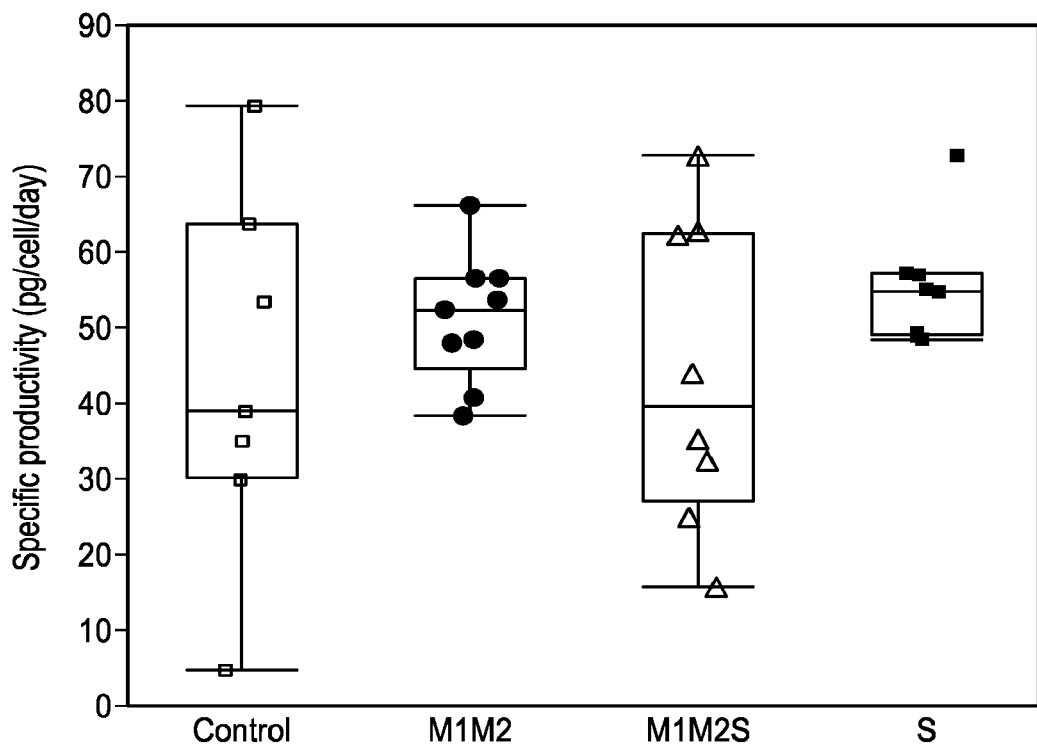
FIG. 5 illustrates the clonal variability in specific productivity of antibody produced during the second fed-batch experiment described in Example 2. Individual clones are designated as described for FIG. 1; the parameters for each box are the same as described for FIG. 1.
Figure 6:
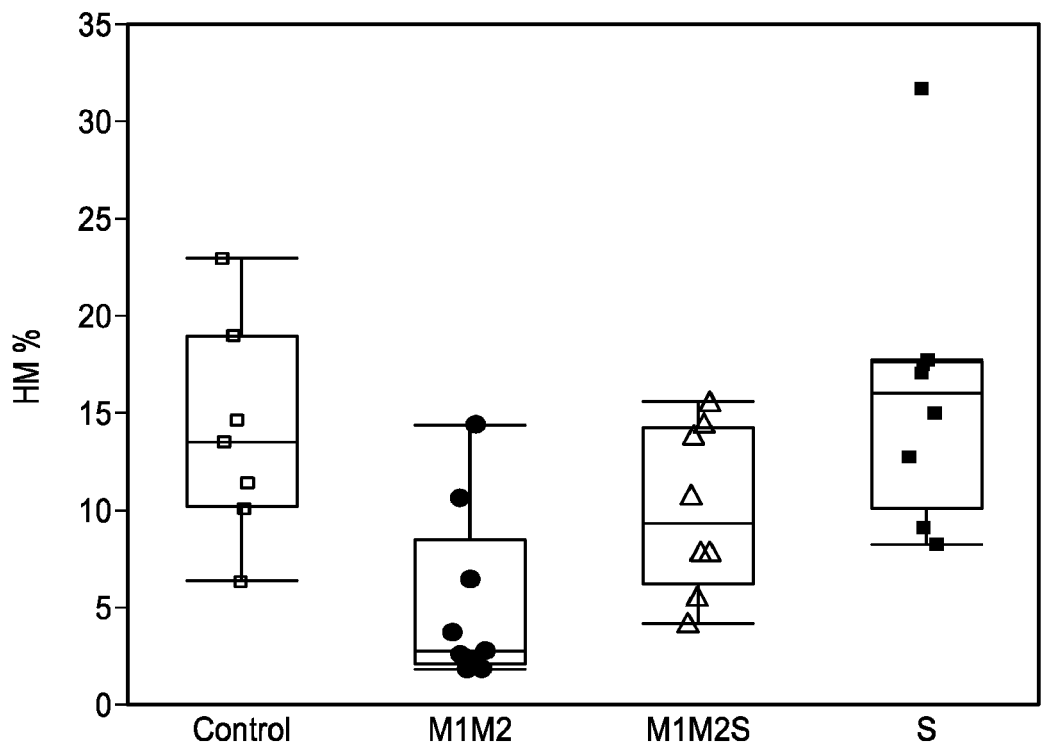
FIG. 6 provides an indication of the clonal variability in percent HM for antibody produced during the second fed-batch experiment described in Example 2. Individual clones are designated as described for FIG. 1; the parameters for each box are the same as described for FIG. 1.

FIGS. 3, 4, and 5 show that the growth and specific productivity were similar between the groups; however titer was significantly increased for the Mgat1 and 2 overexpressing clones as compared to the two other groups. The cell lines overexpressing Mgat1 and Mgat2 (M1M2) as well as those clones overexpressing all three genes (M1M2S) showed a reduction in high mannose levels as compared to the control cells (70% and 29% respectively (FIG. 6). Cell lines overexpressing Slc35a2 (S) however, did not show a statistically significant change when compared to the control (FIG. 6). Since the role of UDP-Galactose Transporter (the protein encoded by Slc35A2) is to transport nucleotide sugar substrate, including UDP-GlcNAc, into the Golgi lumen, increased levels of Slc35a2 will not impact subsequent glycan processing if levels of UDP-GlcNAc are limiting.

The glycoform profiles of the secreted, recombinant MAb B were assessed for each of the overexpressed cell lines (M1M2, M1M2S and S). The M1M2 cell lines showed a significant decrease in all the HM species such as M5, M6, M7 and M8b compared to the control cell lines. Results are shown in Table 5 below.

TABLE 5

Glycosylation profiles of antibody produced in Mgat1, Mgat2 and/or Slc35a2 overexpressing cell lines on day 10 of fed-batch

| Type of Glycoform | Glycoform | Control | M1M2 Clones | M1M2S Clones | S Clones |
|---|---|---|---|---|---|
| High Mannose | M8a | 0.52 | 1 | 0 | 1 |
| | M8b | 0.78 | 0.37 | 0.52 | 0.53 |
| | M7 | 2.65 | 0.58 | 1.25 | 1.24 |
| | M6 | 3.78 | 0.68 | 1.23 | 1.41 |
| | M5 | 7.98 | 1.21 | 4.82 | 10.89 |
| Hybrid | Hybrid | 2.53 | 2.93 | 3.04 | 4.33 |
| Complex | A1G1F | 0.80 | 0.17 | 0.42 | 1.08 |
| | A1G0 | 1.22 | 1.00 | 1.42 | 1.12 |
| | A2G0 | 1.04 | 2.33 | 1.97 | 0.64 |
| | A2G0F | 49.17 | 62.50 | 52.32 | 45.09 |
| | A1G0F | 4.10 | 2.37 | 2.57 | 4.07 |
| | A2G1F | 16.46 | 16.72 | 20.45 | 19.48 |
| | A2G2F | 2.26 | 1.94 | 3.10 | 2.70 |
| | A2G1 | 0.12 | 0.23 | 0.21 | 0.11 |

In control empty vector cell lines, A2G0F was the predominant species (49.17%) among the eight complex glycan species evaluated, followed by A2G1F (16.46%) and other complex glycoforms. A similar trend with respect to the percent of various species was seen for M1M2 and M1M2S. However in case of M1M2 cell lines the amount of A2G0F glycoform was significantly increased by 27% (significance value p=0.0076) as compared to the control. This implies that with the overexpression of Mgat2, there was efficient conversion of hybrid glycan (A1G0M5) to A2G0 and therefore more substrate was available for fucosyltransferase8 (Fut8) to make more A2G0F product as compared to control cell lines. Although overexpression of Slc35a2 did not appear to result in significant increase in the complex glycan levels in this experiment, these results suggest that overexpression of Mgat1 and Mgat2 can increase conversion of HM glycans to complex glycoforms, thereby lowering HM levels.

Example 3

The CHO host cells were transfected with either Mgat1, or Mgat2 individually, or co-transfected with both Mgat1 and Mgat2 expression vectors. After recovery of these cells to greater than 80% viability in selective medium, they were single cell cloned using flow cytometry. A total of 291 clones were analyzed for expression of the genes of Mgat1 and Mgat2. Of these, 48 clones expressing Mgat1 and Mgat2 levels above levels detected in the recombinant CHO cell line expressing a human monoclonal antibody with historically low levels (i.e., <5%) of high-mannose-type glycans (MAb A) were selected, based on good growth and viability.

All 48 clones were grown for at least 60 PDLs (population doubling levels), and during this time course the mRNA expression levels of Mgat 1 and Mgat2 was analyzed at three different time points. Sixteen clones were selected based on stable expression levels of the respective mRNA. To further assess the transfectability of these clones, all 48 clones were transiently transfected with a green fluorescent protein (GFP)-containing vector in a protein-fragment complementation assay, substantially as described by Remy and Michnick (1999), Proc. Natl. Acad. Sci., 96:5394-5399.

Seven clones exhibiting the highest transfection efficiency were selected for further analysis. The Mgat1 and Mgat2 mRNA fold changes of the top seven clones as compared to control CHO is depicted in Table 6.

TABLE 6

Average fold increase in the transcript levels of the Mgat1 and Mgat2

| Clone name | Description | Mgat1 fold increase compared to CHO | Mgat2 fold increase compared to CHO |
|---|---|---|---|
| 18E11 | Mgat2 High | 0.6 | 30.4 |
| 2B8 | Mgat1 Mid | 5.9 | 0.9 |
| 31H7 | Mgat1 and Mgat2 High | 12.4 | 6.3 |
| 38C2 | Mgat1 High | 15.6 | 0.9 |
| 45F2 | Mgat1 High | 20.2 | 0.7 |
| 61A9 | Mgat2 High | 0.5 | 12.7 |
| 63C5 | Mgat1 and Mgat2 High | 14.7 | 15.6 |
| Control | | 0.5 | 1.5 |

A monoclonal antibody that historically exhibited high levels (i.e., >15%) of high-mannose-type glycans (MAb C) was used for transfection in the engineered host cells overexpressing Mgat1 and/or Mgat2 or control non-engineered CHO host cells. Stable pools were created and were chosen for further characterization in a 10 day fed-batch production runs, as described previously. The glycoform profiles and titer of the secreted, recombinant MAb C were assessed for each of the overexpressed cell lines. A significantly lower level of high mannose glycans was detected in host 38C2 as compared to control host for MAb C without impacting the productivity (i.e., titer). Results are shown in Table 7; the values reflect day 10 titer and glycan levels obtained from fed-batch production assay.

TABLE 7

Titer and Glycosylation profiles of unamplified clones expressing MAb C

| Clone name | Titer | % A2G0F | % A2G1F | % A2G2F | % A-fuco | % M5 | HM | p-value for HM |
|---|---|---|---|---|---|---|---|---|
| 18E11 | 0.45 | 63.4 | 18.43 | 2.17 | 85.7 | 4.83 | 5.83 | 0.91 |
| 2B8 | 0.77 | 63.4 | 22.5 | 2.9 | 91.7 | 1.4 | 2.5 | 0.11 |
| 31H7 | 0.9 | 63.37 | 22.9 | 3.03 | 90.7 | 3.5 | 4.77 | 0.54 |
| 38C2 | 0.76 | 63.87 | 23.67 | 2.93 | 92.6 | 0.8 | 1.77 | 0.04* |
| 45F2 | 0.79 | 60.77 | 20.5 | 2.4 | 87.8 | 2.07 | 5.6 | 0.84 |
| 61A9 | 0.7 | 63.33 | 22.43 | 2.77 | 90.1 | 3.93 | 4.93 | 0.6 |
| 63C5 | 0.61 | 65.53 | 21.4 | 2.53 | 91.7 | 1.77 | 2.63 | 0.09 |
| Control | 0.82 | 53.85 | 26.3 | 3.7 | 88.2 | 6.05 | 7.3 | 1 |

Similarly 150 nM and 300 nM amplified pools were generated and analyzed in a 10 day fed-batch production assays. In the case of the 150 nM pools, all the overexpressed host cells exhibited significantly lowered % high mannose as compared to the control host cells without impacting the titer. Results are shown in Tables 8 and 9.

TABLE 8

Titer and Glycosylation profiles of 150 nM amplified clones expressing MAb C

| PQA | Different glycoforms | control | 2B8 | 31H7 | 38C2 | 45F2 |
|---|---|---|---|---|---|---|
| Titer | | 2.82 | 3.53 | 3.72 | 3.39 | 2.78 |
| High Mannose (HM) | HM | 16.2 | 5.55 | 10.6 | 4.17 | 6.73 |
| | M8a | 0.45 | 0.45 | 0.6 | 0.5 | 0.5 |
| | M8b | 0.55 | 0.3 | 0.33 | 0.3 | 0.47 |
| | M7 | 1.4 | 1.05 | 0.8 | 1.07 | 1.77 |
| | M6 | 1.9 | 1.7 | 0.93 | 1.77 | 2.57 |
| | M5 | 11.85 | 2 | 7.93 | 0.53 | 1.43 |

TABLE 8-continued

Titer and Glycosylation profiles of 150 nM amplified clones expressing MAb C

| | | | | | | |
|---|---|---|---|---|---|---|
| Hybrid | Hybrid | 13.75 | 13.2 | 12.37 | 12.93 | 11.75 |
| Complex | A1G1F | 1.3 | 1.15 | 0.13 | 1.2 | 0.87 |
| | A1G0 | 0.8 | 4.7 | 0.83 | 4.7 | 7.2 |
| | A2G0 | 0.75 | 0.8 | 2.03 | 0.77 | 0.67 |
| | A2G0F | 49.25 | 57.35 | 60.03 | 59.9 | 55.63 |
| | A1G0F | 4.15 | 5.25 | 2.7 | 3.53 | 6.9 |
| | A2G1Fa | 9.05 | 7.75 | 7.73 | 8.4 | 6.33 |
| | A2G2F | 2.15 | 1.6 | 1.6 | 1.77 | 1.2 |
| p-value for HM compared to control | | 1 | 0.0008* | 0.0475* | 0.0001* | 0.0011* |

| PQA | Different glycoforms | control | 61A9 | 63C5 | 18E11 |
|---|---|---|---|---|---|
| Titer | | 2.82 | 2.53 | 2.99 | 3.25 |
| High | HM | 16.2 | 6.97 | 6.97 | 10.13 |
| Mannose | M8a | 0.45 | 0.43 | 0.63 | 0.47 |
| (HM) | M8b | 0.55 | 0.2 | 0.6 | 0.15 |
| | M7 | 1.4 | 0.4 | 1.87 | 0.47 |
| | M6 | 1.9 | 0.43 | 2.5 | 0.57 |
| | M5 | 11.85 | 5.6 | 1.4 | 8.53 |
| Hybrid | Hybrid | 13.75 | 12.44 | 11.66 | 10.41 |
| Complex | A1G1F | 1.3 | 0.1 | 0.67 | 0.23 |
| | A1G0 | 0.8 | 0.5 | 3.9 | 0.9 |
| | A2G0 | 0.75 | 1.67 | 1.27 | 5.1 |
| | A2G0F | 49.25 | 63.57 | 60.73 | 62.07 |
| | A1G0F | 4.15 | 2.13 | 3.5 | 1.87 |
| | A2G1Fa | 9.05 | 8.5 | 7.13 | 6.07 |
| | A2G2F | 2.15 | 1.93 | 1.37 | 1.33 |
| p-value for HM compared to control | | 1 | 0.0013* | 0.0013* | 0.0301* |

*indicates P values were significant

With 300 nM amplification, significantly reduced levels of high mannose glycan levels were detected for five pools (61A9, 45F2, 63C5, 38C2, and 2B8), as shown in Table 9.

TABLE 9

Titer and Glycosylation profiles of 300 nM amplified MAb C

| PQA | Different glycoforms | Control | 2B8 | 31H7 | 38C2 | 45F2 |
|---|---|---|---|---|---|---|
| Titer | | 2.59 | 4.39 | 4.63 | 4.69 | 3.48 |
| High | HMN | 19.6 | 6.2 | 11.27 | 6.27 | 8 |
| Mannose | M8a | 0.5 | 0.5 | 0.67 | 0.6 | 0.5 |
| (HM) | M8b | 0.5 | 0.4 | 0.4 | 0.5 | 0.8 |
| | M7 | 1.4 | 1.25 | 0.97 | 1.8 | 2.8 |
| | M6 | 1.8 | 1.8 | 1.13 | 2.77 | 3.6 |
| | M5 | 15.4 | 2.3 | 8.17 | 0.67 | 0.3 |
| Hybrid | Hybrid | 12.4 | 13.15 | 11.93 | 13.13 | 11.6 |
| Complex | A1G1F | 1.1 | 1.2 | 0.1 | 1.4 | 0.8 |
| | A1G0 | 1.1 | 4.35 | 0.87 | 5.27 | 6.85 |
| | A2G0 | 0.8 | 1.15 | 2.07 | 0.9 | 0.75 |
| | A2G0F | 48.8 | 57.15 | 60.13 | 56.83 | 55.15 |
| | A1G0F | 4.7 | 4.7 | 2.77 | 4.13 | 6.85 |
| | A2G1Fa | 7.6 | 7.7 | 7.17 | 7.53 | 5.75 |
| | A2G2F | 1.6 | 1.6 | 1.47 | 1.5 | 1.05 |
| p-value for HM compared to control | | 1 | 0.0119* | 0.1039 | 0.0083* | 0.0283* |

| PQA | Different glycoforms | Control | 61A9 | 63C5 | 18E11 |
|---|---|---|---|---|---|
| Titer | | 2.59 | 2.53 | 3.4 | 3.98 |
| High | HMN | 19.6 | 9.13 | 7.83 | 13.47 |
| Mannose | M8a | 0.5 | 0.5 | 0.87 | 0.47 |
| (HM) | M8b | 0.5 | 0.23 | 0.8 | 0.2 |
| | M7 | 1.4 | 0.5 | 2.1 | 0.63 |
| | M6 | 1.8 | 0.63 | 2.77 | 0.8 |
| | M5 | 15.4 | 7.2 | 1.23 | 11.4 |
| Hybrid | Hybrid | 12.4 | 11.6 | 12.17 | 9.75 |
| Complex | A1G1F | 1.1 | 0.1 | 0.7 | 0.2 |
| | A1G0 | 1.1 | 0.73 | 3.23 | 1.2 |

TABLE 9-continued

Titer and Glycosylation profiles of 300 nM amplified MAb C

| | | | | |
|---|---|---|---|---|
| A2G0 | 0.8 | 2 | 1.13 | 4.7 |
| A2G0F | 48.8 | 62.8 | 59.87 | 60.23 |
| A1G0F | 4.7 | 2.77 | 3.33 | 2.53 |
| A2G1Fa | 7.6 | 7.2 | 7.03 | 5.07 |
| A2G2F | 1.6 | 1.53 | 1.43 | 0.97 |
| p-value for HM compared to control | 1 | 0.0359* | 0.0185* | 0.2835 |

*indicates P values were significant

These results indicate that host cells transformed to overexpress of Mgat1 and/or Mgat2 can be used to prepare recombinant proteins that have increased conversion of HM glycans to complex glycoforms, and hence, lower HM levels.

What is claimed is:

1. A method of decreasing the high mannose glycoform content of a recombinant protein during a mammalian cell culture process, compared to a culture in which mammalian cells are not subject to a transfection to overexpress proteins involved in N-glycosylation, the method comprising:

transfecting a mammalian host cell to overexpress a protein that is involved in an N-glycosylation pathway, wherein the protein involved in the N-glycosylation pathway is selected from the group consisting of N-acetyl-glucosaminyltransferase-1 (encoded by Mgat1); N-acetyl-glucosaminyltransferase-2 (encoded by Mgat2); a UDP-Galactose transporter encoded by Slc35a2; and combinations thereof;

growing the transfected mammalian host cell, thereby producing transfected mammalian host cells; and either (a) subjecting the transfected mammalian host cells to a temperature shift; or (b) inducing the transfected mammalian host cells into cell growth arrest by L-asparagine starvation followed by perfusion with a serum-free perfusion media having an L-asparagine concentration of 5 mM or less, whereby said high mannose glycoform content of the recombinant protein is decreased.

2. The method of claim 1, wherein the temperature shift is from 36° C. to 31° C., or from 36° C. to 33° C.

3. The method of claim 1, wherein the mammalian cell culture process comprises a growth phase and a production phase, wherein the temperature shift occurs at a transition between the growth phase and production phase, or during the production phase.

4. The method of claim 1, wherein the perfusion media has an L-asparagine concentration selected from the group consisting of:

(a) 4.0 mM or less;
(b) 3.0 mM or less;
(c) 2.0 mM or less;
(d) 1.0 mM or less; and
(e) 0 mM.

5. The method of claim 1, wherein the mammalian host cell is transfected to express two or more proteins involved in the N-glycosylation pathway, wherein the proteins are selected from the group consisting of Mgat1 and Mgat2; Mgat1 and Slc35a2; Mgat2 and Slc35a2; and Mgat1, Mgat2 and Slc35a2.

6. The method of claim 5, wherein the mammalian host cell is transfected to express Mgat1 and Mgat2.

7. The method of claim 1, wherein the mammalian host cell has been previously transfected to express the recombinant protein and is subsequently transfected to express a protein that is involved in an N-glycosylation pathway.

8. The method of claim 1, wherein the mammalian host cell is first transfected with a protein that is involved in an N-glycosylation pathway and is subsequently transfected to express the recombinant protein.

9. The method of claim 1, wherein the recombinant protein is selected from the group consisting of a protein comprising an antibody Fc region, a Fc fusion protein, an antibody, an immunoglobulin, and a peptibody.

10. The method of claim 1, wherein high mannose glycoform content of the recombinant protein expressed in the mammalian host cells that have been transfected to overexpress a protein that is involved in N-linked glycosylation is decreased compared to that produced by the mammalian host cell before being transfected to overexpress a protein involved in N-linked glycosylation.

11. The method of claim 1, wherein the high mannose glycoform content of the recombinant protein is less than or equal to 10%.

12. The method of claim 11, wherein the high mannose glycoform content of the recombinant protein is less than or equal to 5%.

13. The method of claim 1, wherein the mammalian cell culture is a perfusion culture.

14. The method of claim 13, wherein the mammalian cell culture is perfused using alternating tangential flow (ATF).

15. The method of claim 13, wherein perfusion begins on or about day 1 to on or about day 9 of the mammalian cell culture, or wherein perfusion begins on or about day 3 to on or about day 7, of the mammalian cell culture.

16. The method of claim 13, wherein perfusion begins when the transfected mammalian host cells have reached a production phase.

17. The method of claim 13, wherein the mammalian cell culture is maintained by fed batch.

18. The method of claim 17, wherein the mammalian cell culture is fed three times or four times during production.

19. The method of claim 1, wherein the mammalian host cell is a Chinese Hamster Ovary (CHO) cell.

20. The method of claim 1, wherein the method further comprises a harvest step for the recombinant protein.

21. The method of claim 20, wherein the harvested recombinant protein is purified and formulated in a pharmaceutically acceptable formulation.

* * * * *